United States Patent
Polzer et al.

(10) Patent No.: US 10,314,780 B2
(45) Date of Patent: Jun. 11, 2019

(54) DRIPPABLE OPTHALMIC BIMATOPROST GEL

(71) Applicant: MEDproject Pharma-Entwicklungs- und Vertriebsgesellschaft mbH, Oberhaching (DE)

(72) Inventors: Heinz Polzer, Weissensberg (DE); Pierre-Paul Elena, Nice (FR); Jürgen Senge, Grünwald (DE)

(73) Assignee: MEDPROJECT PHARMA-ENTWICKLUNGS-UND VERTRIEBSGESELLSCHAFT MBH, Oberhaching (DE)

( * ) Notice: Subject to any disclaimer, the term of this patent is extended or adjusted under 35 U.S.C. 154(b) by 0 days.

(21) Appl. No.: 15/580,770

(22) PCT Filed: Jun. 8, 2016

(86) PCT No.: PCT/EP2016/062990
§ 371 (c)(1),
(2) Date: Dec. 8, 2017

(87) PCT Pub. No.: WO2016/198434
PCT Pub. Date: Dec. 15, 2016

(65) Prior Publication Data
US 2018/0228724 A1    Aug. 16, 2018

(30) Foreign Application Priority Data

Jun. 9, 2015 (EP) .................................... 15171233

(51) Int. Cl.
| | | |
|---|---|---|
| A61K 9/00 | (2006.01) | |
| A61K 47/10 | (2017.01) | |
| A61K 47/32 | (2006.01) | |
| A61P 27/02 | (2006.01) | |
| A61K 31/5575 | (2006.01) | |
| A61K 9/06 | (2006.01) | |

(52) U.S. Cl.
CPC .............. *A61K 9/0048* (2013.01); *A61K 9/06* (2013.01); *A61K 31/5575* (2013.01); *A61K 47/10* (2013.01); *A61K 47/32* (2013.01); *A61P 27/02* (2018.01)

(58) Field of Classification Search
None
See application file for complete search history.

(56) References Cited

U.S. PATENT DOCUMENTS

| | | | | |
|---|---|---|---|---|
| 5,397,567 A | * | 3/1995 | Lobering | A61K 9/0048 424/427 |
| 2006/0211770 A1 | * | 9/2006 | Chang | A61K 9/0048 514/573 |
| 2006/0270735 A1 | * | 11/2006 | Deaciuc | A61K 9/0048 514/530 |
| 2010/0210720 A1 | * | 8/2010 | Pilotaz | A61K 9/0048 514/530 |
| 2011/0319487 A1 | | 12/2011 | Mercier | |

FOREIGN PATENT DOCUMENTS

| | | |
|---|---|---|
| EP | 1275376 A2 | 1/2003 |
| WO | 2012163827 A2 | 12/2012 |

OTHER PUBLICATIONS

Office Communication dated Jan. 30, 2018 in corresponding European application EP15171233.8, 6 pages.
Response to Jan. 30, 2018 Office Communication in corresponding European application EP15171233.8 dated May 14, 2018, 10 pages.
Office Communication acknowledging allowance in corresponding European application EP15171233.8 dated Jul. 16, 2018, 3 pages.

* cited by examiner

*Primary Examiner* — Sreenivasan Padmanabhan
*Assistant Examiner* — Jody L Karol
(74) *Attorney, Agent, or Firm* — Rothwell, Figg, Ernst & Manbeck, P.C.

(57) ABSTRACT

The invention refers to a drippable ophthalmic gel, said gel having composition comprising bimatoprost in an amount of 0.003 to 0.03% by weight, polyacrylate in an amount of >0.2% by weight, povidone (PVP), dextrane, polyethylene glycols (PEG), carboxymethyl cellulose (CMC) or poly (vinyl alcohol) (PVA) in an amount of 0.2 to 10% by weight, an isotonizing agent in an amount to produce an osmolality of 200 to 400 mosml/kg, a salt for adjusting the viscosity in an amount of 0.05 to 0.4% by weight, a base in an amount to adjust the pH to 6 to 8 and excipients normally used in ophthalmic gels, having a viscosity in the range of 200 to 2000 mPa·s.

20 Claims, 2 Drawing Sheets

DRIPPABLE OPTHALMIC BIMATOPROST GEL

CROSS REFERENCE TO RELATED APPLICATION

This application is a 35 U.S.C. 371 National Phase Entry Application from PCT/EP2016/062990, filed Jun. 8, 2016, which claims the benefit of European Patent Application No. 1 5171233.8 filed on Jun. 9, 2015, the disclosure of which is incorporated herein in its entirety by reference.

FIELD OF THE INVENTION

The present invention refers to a drippable ophthalmic bimatoprost gel, wherein said gel having a composition comprising bimatoprost; polyacrylate (carbomer); povidone (PVP), dextrane, polyethylene glycol (PEG) or poly(vinyl alcohol) (PVA); an isotonizing agent; a salt for adjusting the viscosity; a base for adjusting the pH to 6 to 8; excipients normally used in ophthalmic gels and water. Said gel is intended for use as a medicine and for use in the treatment of elevated intraocular pressure (TOP).

BACKGROUND OF THE INVENTION

Currently topically applied prostaglandin analogues are the most recent innovative medications to lower intraocular pressure. Further to their powerful effect on IOP the lack of significant systemic side-effects and the once-daily dosing rapidly placed the prostaglandin analogues among the first line treatments of glaucoma and ocular hypertension. Several agents have been approved formulated as "classical" aqueous eye drops either with preservatives or preservative-free. Apparently bimatoprost shows the greatest efficiency in reducing lOP in this pharmacological class, however, among the most frequently reported common side-effects of this group like conjunctival hyperaemia and irritation, bimatoprost eye drops may have a slightly higher incidence of hyperaemia.

Bimatoprost is a prostaglandin analogue with the chemical (IUPAC) name (Z)-7-[(1R,2R,3R,5S)-3,5-dihydroxy-2-[(E,3S)-3-hydroxy-5-phenylpent-1-enyl]cyclopentyl]-N-ethylhept-5-enamide and the Formula I:

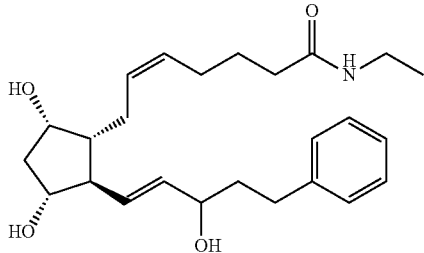

Formula I

The efficiency of a product containing 0.03% by weight of bimatoprost and 0.005% by weight of benzalkonium chloride (preservative) initiated considerable efforts to improve local tolerance by reducing especially the incidence of conjunctival hyperaemia.

EP 1 753 434 discloses a composition comprising from 0.005% to 0.02% bimatoprost by weight and from 100 ppm to 250 ppm benzalkonium chloride, wherein said composition is an aqueous liquid which is formulated for topical administration to the eye.

An alternative method to improve local tolerability and reduce the incidence of topical side effects consists in applying preservative-free eye drops. EP 2 598 117 describes a preservative-free bimatoprost 0.03% solution found to be "non-inferior and equivalent" to preserved bimatoprost 0.03% with a similar safety profile of both products.

EP 2 127 638 and EP 2 178 504 disclose bimatoprost-containing formulations different from the ones of EP 2 598 117. EP 2 127 638 relates to an aqueous ophthalmic solution comprising a PGF2α analogue which solution contains non-ionic surfactant, stabilizing agent, and substantially no preservatives in a container consisting essentially of polyethylene. The PGF2α analogue is selected from the group consisting of latanoprost, isopropyl unoprostone, travoprost, bimatoprost and tafluprost.

EP 2 178 504 discloses an ophthalmic solution without antimicrobial preservative including as active substance at least one prostaglandin and a surfactant as solubilizing agent, characterized in that the solubilizer is polyoxyl-15-hydroxystearate, and characterized in that the prostaglandin concentration in the solution is between 0.02 and 1.5 g/l; The following prostaglandins are named: latanoprost, travoprost, bimatoprost, tafluprost, unoprostone. US 2011/319487 A1 discloses an ophthalmic solution whose active ingredient includes at least one prostaglandin without antimicrobial agents. Moreover, the ophthalmic solution comprises a solubilizing agent, a gelling agent, a carbomer polymerization inhibiting agent and a co-gelling/co-solubilizing agent and shows a viscosity of 8 to 20 mPa*s.

In this context the European pharmacopoeia (Ph. Eur.) rules with respect to formulating topically applied eye medicines: "Eye preparations are sterile . . . Eye-drops may contain excipients, for example, to adjust the tonicity or the viscosity of the preparation, to adjust or stabilise the pH, to increase the solubility of the active substance, or to stabilise the preparation. These substances do not adversely affect the intended medicinal action or, at the concentrations used, cause undue local irritation.

Aqueous preparations supplied in multidose containers contain a suitable antimicrobial preservative in appropriate concentration except when the preparation itself has adequate antimicrobial properties. The antimicrobial preservative chosen must be compatible with the other ingredients of the preparation and must remain effective throughout the period of time during which the eye-drops are in use."

SUMMARY OF THE INVENTION

Object of the present invention is to provide drippable, stable ophthalmic bimatoprost gels according to the rules of the European pharmacopoeia (Ph. Eur.) governing the development, formulation and manufacture of eye preparations and eye drops, allowing for prolonged retention time on the eye to improve their potential efficacy and local tolerability, and to minimize secondary effects in comparison to the state of the art. Moreover, only well-known ingredients already used in eye preparations and standard methods for manufacturing such products had to be employed.

It is essential for gels to be applied to the eye to have the following properties:
to ensure patient compliance, proper and convenient handling of the gels is indispensable, i. e. the viscosity of the gels should be adjusted to a range so that they are drippable from commercially available containers or vials (similar to eye drops and in contrast to eye ointments).

on the other hand the viscosity of the mixture generated from the applied gel drop and the tear film should be in the range tolerated by the eyes.

Therefore, one object of the invention is to develop formulations with the aim of preparing drippable gels having a prolonged retention time on ocular surface which is specifically designed for the active ingredient bimatoprost used in ophthalmology.

The new formulations consider the Ph. Eur. requirements related to the following characteristics:

Tonicity: Salts and/or neutral organic substances in sufficient quantities to adjust osmolality in the tolerance range of the eye, (i. e. approx. 200-400 mosmol/kg), the preferred range is 270-330 mosmol/kg. Since salts with another function than adjusting osmolality may also be contained, their contribution to tonicity must be taken into account requiring appropriate adjustments with the tonicity agents. Very suitable agents to adjust tonicy in polyacrylate-containing ophthalmic gels are organic polyalcohols, like for example mannitol, sorbitol or glycerol. The especially preferred agent is glycerol since the amounts of substance needed are lower than with mannitol or sorbitol because of its lower molecular mass. Glycerol is a liquid whereas mannitol and sorbitol are solids. Thus the formulation contains more liquid and water and comes closer to the natural content in the tear film—a further advantage of glycerol.

Viscosity: Polyacrylate (carbomer) is the principal component generating the viscosity of the gels. According to the present invention, any commercially available types of polyacrylate (carbomer types) may be used. It is useful to choose water-soluble types having a molecular weight of between 1,000,000 and 4,000,000, in the specific case these were carbomer 934, 934P, 940, 941 951, 954, 974, 974P, 980, 981 (cf. H. P. Fiedler, Lexikon der Hilfsstoffe für Pharmazie, Kosmetik and angrenzende Gebiete, $3^{rd}$ edition 1989, Edition Cantor Aulendorf, catchwords: polyacrylic acid, Carbopol).

Since carbomer formulations in terms of viscosities are sensitive to ionic compounds of inorganic and organic origin, a polymeric carrier had to be found which was suitable for stabilizing the "gel structure" and preventing precipitation in the gel. A second polymer is added as carrier (cf. e.g. EP 0562445) to improve stability and manageability in the range of the desired viscosity (200 to 2000 mPa·s; Brookfield RVDV-II Viscometer with SSA 27/13R, spindle SC4-27, 100 rpm, 25° C.). Suitable second polymers are povidone (PVP), dextranes or polyethylene glycols (PEG) or carboxymethyl cellulose (CMC) or poly(vinyl alcohol) (PVA); the most preferred are poly(vinyl alcohol) (PVA) and povidone (PVP).

Viscosity adjustment: Further, the viscosity of the product had to be adjusted in such a way as to allow filling into regular plastic bottles with traditional standard equipment for filling eye drops. Although basically any monovalent salt would achieve this, sodium acetate is preferably used to adjust the viscosity of the formulation according (since this compound is a synthetic impurity in carbomer). Moreover, evidence from manufacturing carbomer gels containing a second polymer showed that fixed amounts of sodium acetate did not consistently yield the viscosity as specified with any commercially available batch of carbomer. This observation is due to the inevitable batch-to-batch variance of carbomer viscosity, although the carbomer starting material complies with the specification.

Adjust or stabilise the pH: Solutions of sodium hydroxide, potassium hydroxide or organic bases are suitable for adjusting the pH to the range tolerated by the eye (pH of about 6 to 8, preferably pH of 7.3). The most preferred organic base is trometamol (tris(hydroxymethyl)-aminomethan) since it is a non-ionic compound which does not affect viscosity by interfering with the polyacrylate gel structure.

Solubiliser (increases the solubility of the active substance): Although solubility of bimatoprost is better than the one of some other prostaglandin analogues, suitable solubilisers facilitate manufacturing and stabilise the finished product. The preferred solubiliser is polysorbate.

Antimicrobial preservative: If a gel contains a preservative, benzalkonium chloride (BAC) is preferred, although the preservatives usually incorporated in eye drops may be used likewise.

Any substance used in the new formulations must be compatible with carbomer (further to the requirements of Ph. Eur.).

It has now be found that it is possible to improve the potential efficacy and to reduce secondary effects in comparison to the state of the art, with a stable drippable ophthalmic gel composition according to claim 1. Even with lower doses of bimatoprost in comparison to the state of the art, a comparable potential efficacy and local tolerability could be reached.

Accordingly, the present invention relates to a drippable ophthalmic gel, said gel comprising 1) bimatoprost in an amount of 0.003 to 0.03% by weight,
2a) polyacrylate (carbomer) in an amount of >0.2% by weight,
2b) povidone (PVP), dextrane, polyethylene glycols (PEG), carboxymethyl cellulose (CMC) or poly(vinyl alcohol) (PVA) in an amount of 0.2 to 10.0% by weight,
3) an isotonizing agent in an amount to produce an osmolality of 200 to 400 mosml/kg, preferably 270 to 330 mosmol/kg,
4) a salt for adjusting the viscosity in an amount of 0.05 to 0.4% by weight,
5) a base in an amount to adjust the pH to 6 to 8, preferably a pH of 7.3,
6) excipients normally used in ophthalmic gels, for example solubilizer and
7) water ("quantum satis"), having a viscosity in the range of 200 to 2000 mPa·s.

Polyacrylate (carbomer) in an amount of >0.2% by weight in the complex mixture is necessary to provide a drippable ophthalmic gel having a viscosity in the range of 200 to 2000 mPa·s.

The content of the ingredients in % by weight refers to the total weight of the ophthalmic gel.

Preferred embodiments of the gel are disclosed in dependent claims 2 to 11.

Preferably, the amount of polyacrylate is in the range of >0.2% to 3.0% by weight, preferably in the range of >0.2% to 0.7% by weight.

Preferably, the gel comprises bimatoprost in an amount of less than 0.01% by weight, more preferably in an amount of less than 0.0045% by weight.

At an amount of less than 0.003% by weight of bimatoprost the effect was insufficient.

Preferably, the gel contains as polyacrylate such types having a molecular weight between 1,000,000 and 4,000,000.

Preferably, the second polymers used are poly(vinyl alcohol) or povidone.

If poly(vinyl alcohol) is used as second polymer in an amount of 0.2 to 0.8%, it is preferably a completely hydrolyzed grade, i.e. the degree of hydrolysis is at least 99% and the molecular weight is between 15,000 and 200,000.

If the second polymer is povidone (polyvinylpyrrolidone or PVP), the gel preferably comprises povidone in an amount of >0.8 to 10.0% by weight; more preferably, povidone in an amount of >2.5 to 10% by weight, because these gels surprisingly showed a better effect than gels with poly(vinyl alcohol) as second polymer (cf. Table 2 and FIG. 2). Preferably, the povidone is of the type K25 or type K30.

Preferably, the gel further comprises sorbitol, mannitol or glycerol in an amount of 1.2 to 5.5% by weight as an isotonizing agent to produce an osmolality of 200 to 400 mosml/kg, preferably 270 to 330 mosmol/kg. More preferably, the isotonizing agent is glycerol in an amount of 1.2 to 3% by weight, most preferably with 2% by weight.

Preferably the gel comprises a base in an amount of 0.1 to 0.8% by weight to adjust the pH to 6 to 8, preferably to a pH of 7.3.

Preferably, the base is trometamol, i.e. Tris(hydroxymethyl)-aminomethan.

Preferably, the gel is preservative-free.

Preferably, the gel contains antimicrobial preservatives as excipients.

Preferably, the preserved gel comprises benzalkonium chloride as a preservative, more preferably in the range of 0.005 to 0.02% by weight.

Moreover, the gel according to the present invention features a viscosity of 200 to 2000 mPa·s (Brookfield Viscometer). It is intended for use as a medicine and for use in the treatment of elevated intraocular pressure.

Excipients, i.e. any substance used in the new formulations must be compatible with carbomer (further to the requirements of Ph. Eur.), and preferably a well-known ingredient of eye preparations.

Manufacturing Process

Preferably the gel is compounded in a vessel with built-in stirrer(s). It is equipped for working in vacuo and sterilisation by saturated steam. Sterilisation of the finished gel product can be done by steam sterilisation. Alternatively the mixed solutions of excipients resistant to the conditions of the process are steam sterilised, and the solution with bimatoprost plus solubiliser, if any, and the solutions of excipients not resistant to steam sterilisation are added to the previously steam sterilised mixed solutions of excipients by membrane filtration (the standard procedure to sterilise aqueous eye-drops of low viscosity).

Finally, the sterilised finished product is aseptically filled into pre-sterilised multidose plastic containers, respectively into (sterile) single-dose containers, if the eye gel is unpreserved, i.e. for example without benzalkonium chloride (BAC).

EXAMPLE 1

Figure 1:
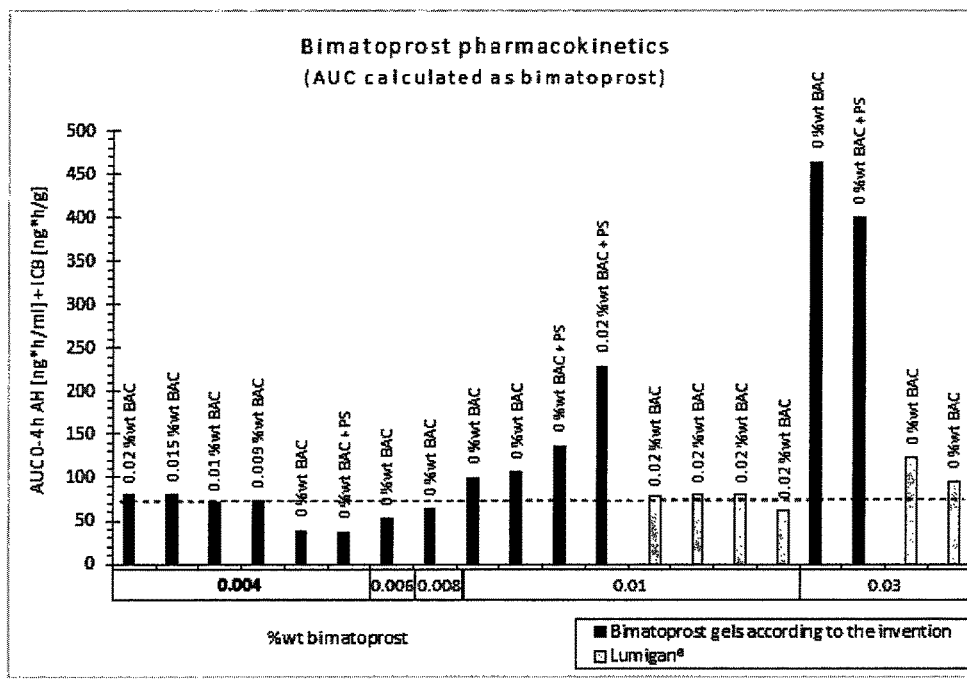
FIG. 1 is a chart of the bimatoprost pharmacokinetics with a comparison of the AUC (Area under the curve) values of the gel according to the invention (black bars) in comparison to the state of the art (grey bars).

Preserved bimatoprost 0.004% gel containing poly(vinyl alcohol):
Solution A: Dissolve 1.6 g poly(vinyl)alcohol in 30.4 g purified water by heating to 95° C. while mixing.
Solution B: Dissolve 1.05 g trometamol in 10 g purified water.
Solution C: Dissolve 8 mg bimatoprost, 4 ml benzalkonium chloride 1% solution, 4.8 g glycerol, 0.44 g sodium acetate·3 $H_2O$ in 90 g purified water, and finally disperse 0.70 g carbomer.
Combine Solution C with Solution A, then add Solution B and complete with purified water to the final weight of 200.0 g. Mix during 30 minutes. Autoclave the mixture for 20 min at 121-124° C. Use vacuum degassing equipment, if necessary to obtain a bubble-free gel.

The gel is clear, transparent and uncoloured, has a pH of 7.47, a viscosity of 450 mPa·s, and an osmolality of 291 mosm/kg

EXAMPLE 2

Unpreserved bimatoprost 0.004% gel containing poly (vinyl alcohol):
Solution A: Dissolve 0.8 g poly(vinyl)alcohol in 15.2 g purified water by heating to 95° C. while mixing.
Solution B: Dissolve 0.5 g trometamol in 10 g purified water.
Solution C: Dissolve 4 mg bimatoprost, 50 µl polysorbate 80, 2.4 g glycerol, 0.22 g sodium acetate·3 $H_2O$ in 45 g purified water, and finally disperse 0.35 g carbomer.
Combine Solution C with Solution A, then add Solution B and complete with purified water to the final weight of 100.0 g. Mix during 30 minutes. Autoclave the mixture for 20 min at 121-124° C. Use vacuum degassing equipment, if necessary to obtain a bubble-free gel.

The gel is clear, transparent and uncoloured, has a pH of 7.30, a viscosity of 422.5 mPa·s, and an osmolality of 295 mosm/kg.

EXAMPLE 3

Preserved bimatoprost 0.004% gel containing povidone:
Solution A: Dissolve 4.0 g povidone and 1.02 g trometamol in 40 g purified water.
Solution B: Dissolve 8.4 mg bimatoprost (5% overage) in 5 g purified water.
Mixture C: Dissolve 0.37 g sodium acetate·3 $H_2O$, 4 ml benzalkonium chloride 1% solution, and 4.6 g glycerol in 80 g purified water, then disperse 0.7 g carbomer. Use a total of 10 g purified water in suitable portions to rinse the containers during the addition steps. Agitate the mixture during 30 minutes, then autoclave Mixture C for 20 min at 121-124° C.
Preparation of the finished gel: Add Solution B to Mixture C through a sterile membrane filter (pore size 0.22 µm), rinse with purified water, then add Solution A through a sterile membrane filter (pore size 0.22 µm), rinse with purified water; use a total of 30 g purified water divided in suitable portions to rinse the containers and membrane filters during the addition steps. Eventually complete the procedure with purified water by adjusting to the final weight of 200.0 g.
Use vacuum degassing equipment, if necessary to obtain a bubble-free gel.

The gel is clear, transparent, very pale yellow, and has a pH of 7.20, a viscosity of 465 mPa·s, and an osmolality of 295 mosm/kg.

EXAMPLE 4

Unpreserved bimatoprost 0.004% gel containing polyvinylpyrrolidone:
Solution A: Dissolve 4.0 g povidone and 1.02 g trometamol in 30 g purified water.
Solution B: Dissolve 8.4 mg bimatoprost (5% overage) in 5 g purified water.
Mixture C: Dissolve 0.37 g sodium acetate·3 $H_2O$, and 4.6 g glycerol in 80 g purified water, then disperse 0.7 g carbomer. Use a total of 10 g purified water in suitable portions to rinse the containers during the addition steps. Agitate the mixture during 30 minutes, then autoclave Mixture C for 20 min at 121-124° C.
Preparation of the finished gel: Add Solution B to Mixture C through a sterile membrane filter (pore size 0.22 μm), rinse with purified water, then add Solution A through a sterile membrane filter (pore size 0.22 μm), rinse with purified water; use a total of 30 g purified water divided in suitable portions to rinse the containers and membrane filters during the addition steps. Eventually complete the procedure with purified water by adjusting to the final weight of 200.0 g.
Use vacuum degassing equipment, if necessary to obtain a bubble-free gel.
The gel is clear, transparent, very pale yellow, and has a pH of 7.22, a viscosity of 467.5 mPa·s, and an osmolality of 292 mosm/kg.

Pharmacokinetic Studies in Rabbits

Pharmacokinetic studies in rabbits generally provide non-clinical confirmation that formulations with different composition could perform comparably to the approved state of the art preparation Lumigan® (cf. "Assessment report for Lumigan®" (Ref: EMA/105752/2010)).

The composition of Lumigan® 0.1 mg/ml eye drops is as follows:

Bimatoprost 0.1 mg/ml, Benzalkonium chloride 0.2 mg/ml, Sodium chloride, Sodium phosphate dibasic heptahydrate, Citric acid monohydrate, Hydrochloric acid or sodium hydroxide (to adjust pH), Purified water.

The composition of Lumigan® 0.3 mg/ml eye drops is as follows:

Bimatoprost 0.3 mg/ml, Benzalkonium chloride 0.05 mg/ml, Sodium chloride, Sodium phosphate dibasic heptahydrate, Citric acid monohydrate, Hydrochloric acid or sodium hydroxide (to adjust pH), Purified water.

Ocular absorption of bimatoprost as determined in aqueous humour and the iris-ciliary body is an accepted measure of "ocular bioavailability" which allows assessing the clinical efficacy. Various bimatoprost-containing eye gels have been tested in the following design:

Pigmented rabbits (HY79b strain), 6 per group, 3 per point in time received a single instillation of 30 μl in right and left eyes. 1 and 4 hours after the administration aqueous humour (AH) and iris-ciliary body (ICB) samples are taken from both treated eyes. Assay of bimatoprost and bimatoprost acid (the major active metabolite of bimatoprost) in the AH and ICB samples yields concentration profiles used to calculate the area under the curve (AUC) between 0 and 4 h. In ocular pharmacokinetics, AUC is determined in plots of concentration of drug in AH and ICB. The concentration is measured at defined points in time, and the trapezoidal rule is used to calculate AUC as concentration * time (unit [ng*h/ml] in AH and [ng*h/g] in ICB). Contents of bimatoprost and bimatoprost acid, transferred to bimatoprost, were added for each point in time prior to the calculation of the AUC 0-4. The columns "AUC 0-4 h" in Table 1 and Table 2 show the results (cf. FIG. 1 and FIG. 2), which can be considered as an equivalent for the amount of drug substance penetrated into the ocular tissues.

TABLE 1

| Product | % Bim | % BAC | % Polysorbate | AUC 0-4 h | Ratio vs Lum 0.03% | Ratio vs Lum 0.01% |
| --- | --- | --- | --- | --- | --- | --- |
| Gel with PVA | 0.004 | 0.02 | 0 | 80.3044 | 0.73 | 1.06 |
| Gel with PVA | 0.004 | 0.015 | 0 | 80.8389 | 0.74 | 1.07 |
| Gel with PVA | 0.004 | 0.01 | 0 | 71.1765 | 0.65 | 0.94 |
| Gel with PVA | 0.004 | 0.009 | 0 | 73.9179 | 0.68 | 0.98 |
| Gel with PVA | 0.004 | 0 | 0 | 38.2796 | 0.35 | 0.51 |
| Gel with PVA | 0.004 | 0 | 0.05 | 36.3144 | 0.33 | 0.48 |
| Gel with PVA | 0.006 | 0 | 0 | 52.7179 | 0.48 | 0.70 |
| Gel with PVA | 0.008 | 0 | 0 | 63.7572 | 0.58 | 0.85 |
| Gel with PVA | 0.01 | 0 | 0 | 99.0791 | 0.91 | 1.31 |
| Gel with PVA | 0.01 | 0 | 0 | 105.8715 | 0.97 | 1.40 |
| Gel with PVA | 0.01 | 0 | 0.05 | 136.3845 | 1.25 | 1.81 |
| Gel with PVA | 0.01 | 0.02 | 0.05 | 228.9203 | 2.09 | 3.03 |
| Lumigan ® 0.01% | 0.01 | 0.02 | 0 | 77.9388 | 0.71 | 1.03 |
| Lumigan ® 0.01% | 0.01 | 0.02 | 0 | 80.3515 | 0.73 | 1.07 |
| Lumigan ® 0.01% | 0.01 | 0.02 | 0 | 80.8019 | 0.74 | 1.07 |
| Lumigan ® 0.01% | 0.01 | 0.02 | 0 | 62.6922 | 0.57 | 0.83 |
| Gel with PVA | 0.03 | 0 | 0 | 464.0063 | 4.24 | 6.15 |
| Gel with PVA | 0.03 | 0 | 0.05 | 400.1780 | 3.66 | 5.30 |
| Lumigan ® 0.03% | 0.03 | 0 | 0 | 123.5723 | 1.13 | 1.64 |
| Lumigan ® 0.03% | 0.03 | 0 | 0 | 95.2608 | 0.87 | 1.26 |

In the sixth and seventh column the ratio of AUC vs average AUC of Lumigan® 0.3 mg/ml (=Lum 0.03% wt.) (preservative-free) and the ratio of AUC vs average AUC of Lumigan® 0.1 mg/ml (=Lum 0.01% wt.) are indicated. Table 2 shows the same lay-out, however, the sixth column Ratio vs Lum 0.03% of Table 1 is replaced by Content of PVP in Table 2.

TABLE 2

| Product | % Bim | % BAC | % Polysorbate | AUC 0-4 h | Content of PVP | Ratio vs Lum 0.01% |
|---|---|---|---|---|---|---|
| Gel with PVA | 0.01 | 0 | 0 | 77.7524 | — | 1.50 |
| Gel with PVP | 0.0105 | 0 | 0 | 220.7574 | 2% | 4.25 |
| Gel with PVP | 0.0105 | 0 | 0 | 202.2001 | 2% | 3.89 |
| Lumigan® 0.01% | 0.01 | 0.02 | 0 | 62.6922 | — | 1.21 |
| Lumigan® 0.01% | 0.01 | 0.02 | 0 | 41.2092 | — | 0.79 |
| Gel with PVP | 0.0305 | 0.005 | 0 | 611.3325 | 2% | 11.77 |
| Lumigan® 0.03% | 0.03 | 0.005 | 0 | 195.1924 | — | 3.76 |

Figure 2:
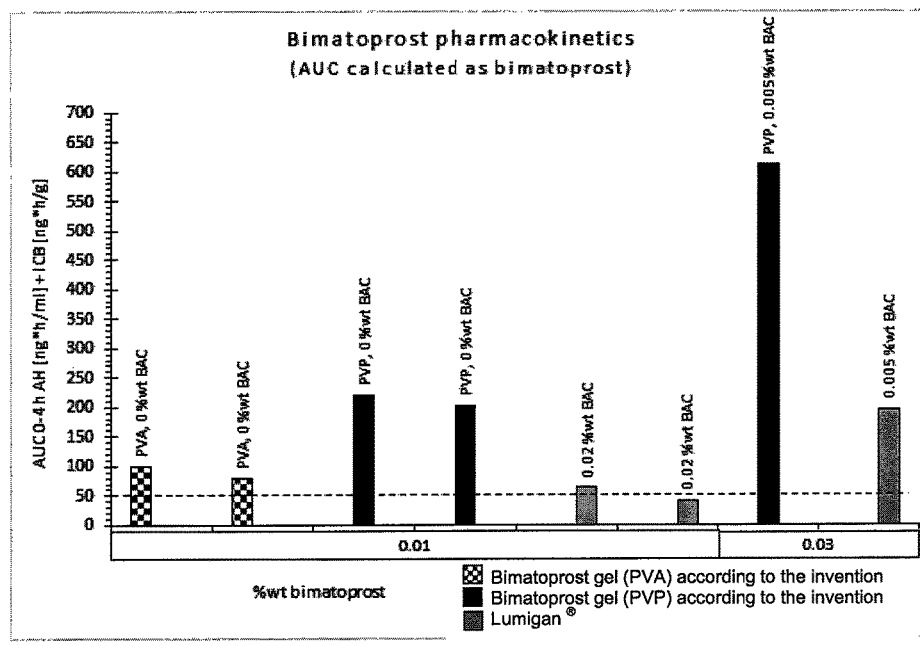
FIG. 2 shows AUC-values to compare gels according to the invention containing poly (vinyl alcohol) (PVA) (dotted bars) or polyvinylpyrrolidone (PVP) (black bars) with the state of the art (grey bars).

In FIGS. 1 and 2, AUC-values are plotted on the vertical axis and different bimatoprost concentrations are plotted on the horizontal axis. Above each bar the different amount of benzalkonium chloride (BAC) is plotted. An amount of 0.02% by weight (0.02% wt) means an amount of 200 ppm with respect to the bimatoprost composition. E.g. in the leftmost composition, the amount of BAC is 200 ppm. In FIGS. 1 and 2 the dotted line represents the average AUC of the samples of Lumigan® 0.01% tested (mean values: 75.44 in FIG. 1 and 51.95 in FIG. 2).

In FIG. 1, the bimatoprost gels according to the invention, which further comprises 0.05% wt of polysorbate 80 (PS), are marked with "+PS" above the corresponding bar.

The surprising result is that, based on the bimatoprost concentrations, the gels achieve a two-to threefold increase in ocular bioavailability of bimatoprost compared with Lumigan®. Various bimatoprost gels with only 40% of the preparation Lumigan® 0.01% provide essentially similar ocular bioavailability (cf. FIG. 1). As it can be seen in FIG. 1, the gels according to the invention (black bars) with an amount of only 0.004% by weight of bimatoprost show comparable AUC-values to the AUC-values of the state of the art preparation Lumigan® (grey bars and dotted line for average values of Lumigan® 0.01%) with a higher concentration of bimatoprost (0.01 and even 0.03% by weight).

Moreover, the gels according to the invention with a concentration of 0.01% by weight and without BAC (0 ppm) show increased AUC-values in comparison to Lumigan® with the same 0.01% by weight concentration and 200 ppm of BAC.

The most pronounced effect could be seen at the comparison between the 0.03% by weight of the prepartion of Lumigan® with the gels according to the invention. A threefold increase in ocular bioavailability of bimatoprost compared with the preparation of Lumigan® could be observed (four bars on the right end of the charts in FIG. 1).

Even more surprising (cf. FIG. 2), the gels according to the invention with povidone as second polymer (black bars) containing the same amount of bimatoprost (0.01% by weight) as the state of the art preparation Lumigan® (grey bars and dotted line for average values of Lumigan® 0.01%) and the bimatoprost gel with poly(vinyl)alcohol as second polymer (dotted black bars) show AUC-values around four times as high as the AUC-values of Lumigan® and 1.5 times as high as the AUC-values of bimatoprost gel with poly (vinyl)alcohol. With a higher concentration of bimatoprost (0.03% by weight) a threefold increase in ocular bioavailability of bimatoprost could be observed for the preserved bimatoprost gel with povidone as second polymer compared with the preserved reference preparation Lumigan® (two bars on the right end of the charts in FIG. 2).

Obviously the new gel vehicle supports penetration of bimatoprost into ocular tissues much more effectively than the one of Lumigan®'s "clear, isotonic, colourless, sterile ophthalmic solution".

The ocular tolerability investigated in a rabbit model in terms of chemosis, tearing, corneal opacity, and conjunctival redness, was equal for any of the products indicated in Table 1 and 2 and in the Figures.

The invention claimed is:

1. A drippable ophthalmic gel, said gel comprising
   1) bimatoprost in an amount of 0.003 to 0.03% by weight,
   2a) polyacrylate in an amount of >0.2% by weight,
   2b) povidone, dextrane, polyethylene glycol, carboxymethyl cellulose or poly(vinyl-alcohol) in an amount of 0.2 to 10.0% by weight,
   3) an isotonizing agent in an amount to produce an osmolality of 200 to 400 mosml/kg,
   4) a salt for adjusting the viscosity in an amount of 0.05 to 0.4% by weight,
   5) a base in an amount to adjust the pH to 6 to 8,
   6) excipients normally used in ophthalmic gels, and
   7) water, and having a viscosity in the range of 200 to 2000 mPa·s, measured with a Brookfield RVDV-II Viscometer at 25° C.

2. The drippable ophthalmic gel according to claim 1 characterized in that the amount of polyacrylate is in the range of >0.2% to 3.0% by weight.

3. The drippable ophthalmic gel according to claim 1, characterized in that the amount of povidone is in the range of >0.8% to 10% by weight.

4. The gel according to claim 1, characterized in that the amount of bimatoprost is less than 0.01% by weight.

5. The gel according to claim 1, characterized by comprising sorbitol, mannitol or glycerol as an isotonizing agent in an amount of 1.2 to 5.5% by weight.

6. The gel according to claim 1, characterized by comprising a base in an amount of 0.1 to 0.8% by weight.

7. The gel according to claim 1, characterized in that the base is trometamol.

8. The gel according to claim 1, characterized by containing as the polyacrylate such types having a molecular weight between 1,000,000 and 4,000,000.

9. The gel according to claim 1, characterized by comprising no preservative.

10. The gel according to claim 1, characterized by comprising benzalkonium chloride as a preservative.

11. The gel according to claim 10, characterized in that the amount of benzalkonium chloride is in the range of 0.005 to 0.02% by weight.

12. A single-dose container containing the drippable ophthalmic gel according to claim 1, wherein the drippable ophthalmic gel is preservative-free.

13. A multidose plastic container containing the drippable ophthalmic gel according to claim 1, wherein the drippable ophthalmic gel contains a preservative.

14. A method of making the drippable ophthalmic gel according to claim 1, comprising the following steps:
   A) dissolving 2b) in 7) and heating while mixing;
   B) dissolving 5) in 7),
   C) dissolving 1), 3), 4), and 6) in 7) and then disperse 2a) therein,
   D) combining C) with A) to form a mixture, then adding B) to the mixture, and then adding 7) thereto.

15. A method of treating a subject suffering from elevated intraocular pressure, comprising administering the drippable ophthalmic gel of claim 1 to said subject, thereby reducing elevated intraocular pressure in said subject.

16. The drippable ophthalmic gel of claim 1, wherein the drippable ophthalmic gel comprises the isotonizing agent in an amount to produce an osmolality of 270 to 330 mosmol/kg.

17. The drippable ophthalmic gel of claim 1, wherein the base is in an amount to adjust the pH to 7.3.

18. The drippable ophthalmic gel of claim 1, wherein the amount of polyacrylate is in the range of >0.2% to 0.7% by weight.

19. The drippable ophthalmic gel of claim 1, wherein the amount of povidone is in the range of >2.5% to 10% by weight.

20. The drippable ophthalmic gel of claim 1, wherein the amount of bimatoprost is less than 0.0045% by weight.

* * * * *